(12) United States Patent
Sinderby (10) Patent No.: US 6,588,423 B1
(45) Date of Patent: Jul. 8, 2003

(54) METHOD AND DEVICE RESPONSIVE TO MYOELECTRICAL ACTIVITY FOR TRIGGERING VENTILATORY SUPPORT

(75) Inventor: Christer Sinderby, Montreal (CA)

(73) Assignee: Universite de Montreal, Montreal (CA)

( * ) Notice: Subject to any disclaimer, the term of this patent is extended or adjusted under 35 U.S.C. 154(b) by 0 days.

(21) Appl. No.: 09/623,061

(22) PCT Filed: Feb. 26, 1998

(86) PCT No.: PCT/CA99/00180

§ 371 (c)(1),
(2), (4) Date: Jun. 22, 2001

(87) PCT Pub. No.: WO99/43374

PCT Pub. Date: Sep. 2, 1999

(30) Foreign Application Priority Data

Feb. 27, 1998 (CA) .............................................. 2230857

(51) Int. Cl.[7] .............................................. F16K 31/02
(52) U.S. Cl. ............................ 128/204.23; 128/204.21; 128/204.26; 128/200.24
(58) Field of Search ..................... 128/200.24, 204.18, 128/204.21, 204.23, 204.26, 205.24, 207.14, 207.16, 207.18, 898

(56) References Cited

U.S. PATENT DOCUMENTS

| 4,932,402 | A | * | 6/1990 | Snook et al. ......... | 128/204.23 |
| 5,074,299 | A | * | 12/1991 | Dietz ..................... | 128/204.21 |
| 5,353,788 | A | | 10/1994 | Miles .................... | 128/204.23 |
| 5,513,631 | A | | 5/1996 | McWilliams ........... | 128/204.23 |
| 5,520,192 | A | | 5/1996 | Kitney et al. | |
| 5,671,752 | A | | 9/1997 | Sinderby et al. | |
| 5,692,497 | A | * | 12/1997 | Schnitzer et al. ...... | 128/204.21 |
| 6,357,438 | B1 | * | 3/2002 | Hansen .................. | 128/204.18 |

FOREIGN PATENT DOCUMENTS

| DE | 94 06 407 | 9/1995 |
| EP | 0 678 304 | 10/1995 |
| EP | 0 684 048 | 11/1995 |
| EP | 0 714 670 | 6/1996 |
| WO | 98/48877 | 5/1998 |

\* cited by examiner

Primary Examiner—Glenn K. Dawson
(74) Attorney, Agent, or Firm—Charles N. Quinn (57) ABSTRACT

A method and device for triggering ventilatory support to assist the patient's respiration. Myoelectrical activity of a patient's respiratory-related muscle is sensed to detect respiratory effort, and to produce a myoelectrical signal representative of the sensed muscle myoelectrical activity. Respiratory flow and pressure can also be measured to produce respective respiratory pressure and respiratory flow signals. A logic trigger circuit triggers ventilatory support in relation to the myoelectrical signal, respiratory flow signal and/or respiratory pressure signal to assist respiration of the patient. The amplitude of the myoelectrical signal is compared to a given threshold, and ventilatory support is triggered when the amplitude of the myoelectrical signal is higher than this threshold. Increment of myoelectrical signal amplitude can also be detected to trigger ventilatory support, while decrement of the myoelectrical signal amplitude can be detected to request non-triggering of the ventilatory support.

24 Claims, 10 Drawing Sheets

METHOD AND DEVICE RESPONSIVE TO MYOELECTRICAL ACTIVITY FOR TRIGGERING VENTILATORY SUPPORT

BACKGROUND OF THE INVENTION

1. Field of the Invention

The present invention relates to a method and device for triggering lung ventilatory support in response to myoelectrical activity of the diaphragm (or other inspiratory-related muscle), or in response to myoelectrical activity of the diaphragm (or other inspiratory-related muscle), inspiratory flow and/or inspiratory pressure in combination.

2. Brief Description of the Prior Art

Triggering of ventilatory support using airway inspiratory flow and/or pressure is affected by many factors including:

inspiratory muscle function, i.e. how activation is translated into tension, and how tension is translated into pressure; and respiratory mechanics such as the elastic and resistive components of the respiratory system.

A drawback of the prior art airway inspiratory flow and/or pressure based ventilatory support triggering systems is that they cannot adequately detect inspiratory efforts in, for example, patients suffering from severe airflow limitation.

OBJECTS OF THE INVENTION

An object of the present invention is to use myoelectrical activity of the diaphragm or other respiratory-related muscles to trigger ventilatory support and/or to end the ventilatory support, in view of eliminating inspiratory flow and/or pressure trigger function related problems due to impedance of the ventilatory support system and the respiratory system. The present invention will also eliminate the problems related to leaks in the air flow system (infants).

Another object of the present invention is to provide a ventilatory support triggering method and device responsive to a combination of myoelectrical activity with inspiratory flow and/or pressure to guarantee adequate triggering of the ventilatory support apparatus in the eventual presence of delayed onset or absence of myoelectrical activity of the diaphragm or other respiratory-related muscle. The ventilatory support triggering method and device will improve detection of inspiratory efforts without jeopardizing the patient's ability to use muscles other than the diaphragm to trigger the ventilatory support system.

A further object of the present invention is to provide a ventilatory support triggering method and device capable of triggering any ventilatory support system, and of triggering any mode of ventilatory support.

SUMMARY OF THE INVENTION

The present Invention relates to a method and device for triggering a ventilatory support apparatus in response to a respiratory effort via the use of myoelectrical activity of the diaphragm (or other muscles associated with respiratory effort) as well as a method and device for triggering a ventilatory support apparatus in response to a respiratory effort based on the combined use of myoelectrical activity of the diaphragm (or other muscles associated with respiratory effort) with respiratory flow and/or pressure.

More specifically, according to the present invention, there is provided a method for triggering ventilatory support from a ventilatory apparatus connected to a patient's respiratory system to assist inspiration of the patient, comprising the steps of:

sensing myoelectrical activity of an respiratory-related muscle of the patient, to thereby detect respiratory effort of this patient;

producing a myoelectrical signal representative of the sensed muscle myoelectrical activity, and triggering ventilatory support in relation to the myoelectrical signal to assist inspiration of the patient in response to respiratory effort of the patient.

In accordance with preferred embodiments:

the method for triggering ventilatory support further comprises the step of filtering from the myoelectrical signal at least one of the following disturbances: motion artifacts, ECG, electrical interference, and high frequency noise;

the triggering step comprises comparing an amplitude of the myoelectrical signal to a given threshold, and triggering ventilatory support when the amplitude of the myoelectrical signal is higher than the given threshold:

the triggering step comprises detecting an increment of an amplitude of the myoelectrical signal, and triggering ventilatory support in response to detection of this increment;

the method for triggering ventilatory support further comprises the steps of detecting decrement of an amplitude of the myoelectrical signal, and requesting non-triggering of the ventilatory support in response to that decrement;

the method for triggering ventilatory support comprises detecting the level of noise in the myoelectrical signal, and determining whether the respiratory-related muscle of the patient is active in relation to the detected level of noise; and the sensing step comprises sensing myoelectrical activity of the respiratory-related muscle on two opposite sides of the center of a depolarizing region of this respiratory-related muscle, and the producing step comprises (a) generating two myoelectrical signal components in response to sensing of the myoelectrical activity of the respiratory-related muscle on the two opposite sides of the center of the depolarizing region, respectively, these two myoelectrical signal components having reversed polarities, (b) subtracting the two myoelectrical signal components from each other to produce a subtraction signal, (c) adding the two myoelectrical signal components to each other to produce an addition signal, (d) multiplying the addition signal by a predetermined constant to produce a multiplied signal, (e) comparing the multiplied signal to the subtraction signal, and (f) if the subtraction signal has an amplitude higher then an amplitude of the multiplied signal, accepting the subtraction signal as myoelectrical signal.

The present invention also relates to a method for triggering ventilatory support from a ventilatory apparatus connected to a patient's respiratory system to assist inspiration of the patient, comprising the steps of:

sensing myoelectrical activity of an respiratory-related muscle of the patient to detect respiratory effort of the patient, and producing a myoelectrical signal representative of the sensed muscle myoelectrical activity;

measuring respiratory flow of the patient, and producing a respiratory flow signal;

measuring respiratory pressure of the patient, and producing a respiratory pressure signal; and triggering ventilatory support in relation to the myoelectrical signal, respiratory flow signal and/or respiratory pressure signal to assist inspiration of the patient in response to respiratory effort of this patient.

Also in accordance with the present invention, there is provided a device for triggering ventilatory support from a ventilatory apparatus connected to a patient's respiratory system to assist inspiration of said patient, comprising: sensor means for sensing myoelectrical activity of a respiratory-related muscle of the patient, to thereby detect respiratory effort of the patient; means for producing a myoelectrical signal representative of the sensed muscle myoelectrical activity; and means for triggering ventilatory support in relation to the myoelectrical signal to assist inspiration of the patient in response to respiratory effort of the patient.

According to a further aspect of the subject invention, there is provided a device for triggering ventilatory support from a ventilatory apparatus connected to a patient's respiratory system to assist respiration of said patient, comprising a sensor for sensing myoelectrical activity of a respiratory-related muscle of the patient, to thereby detect respiratory effort of the patient, a signal processor for producing a myoelectrical signal representative of the sensed muscle myoelectrical activity, and a trigger circuit for triggering ventilatory support in relation to the myoelectrical signal to assist inspiration of the patient in response to respiratory effort of the patient.

Finally, the present invention relates to a device for triggering ventilatory support from a ventilatory apparatus connected to a patient's respiratory system to assist respiration of the patient, comprising a myoelectrical activity sensor for sensing myoelectrical activity of a respiratory-related muscle of the patient to detect respiratory effort of the patient, and producing a myoelectrical signal representative of the sensed muscle myoelectrical activity, a respiratory flow detector for measuring respiratory flow of the patient, and producing a respiratory flow signal, a respiratory pressure detector for measuring respiratory pressure of the patient, and producing a respiratory pressure signal, and a logic trigger circuit for triggering ventilatory support in relation to the myoelectrical signal, respiratory flow signal and/or respiratory pressure signal to assist inspiration of the patient in response to respiratory effort of the patient.

For instance, the diaphragm electromyogram (EMG) represents the motor unit recruitment and firing rate and hence the inspiratory effort of the diaphragm which normally is the principal inspiratory muscle. Other muscles, for example parasternal intercostal muscles, sternocleidomatoids, scalenes, alae nasi, etc., associated with inspiratory efforts can also be useful sources for determining the onset of an inspiratory effort. The inspiratory flow and/or pressure also represent a source of global inspiratory effort, i.e. the inspiratory effort made by all chest wall muscles participating in the inspiration. The pressure can be replaced by direct measurements of transpulmonary, transabdominal or transadiaphragmatic pressures. An inspiratory effort can be first detected by the diaphragm EMG and an instant later as inspiratory flow and/or pressure. However, limitations of both methods to detect a breathing effort may occur depending on the condition of the patient. One limitation of using the diaphragm EMG is that under certain conditions, inspiratory muscles other than the diaphragm may initiate the inspiration, such that diaphragm EMG occurs later than inspiratory flow and/or pressure. One limitation of using airway inspiratory flow and/or pressure measurements is that under certain conditions, the inspiratory effort is not revealed by such measurements and consequently the ventilatory support apparatus is not triggered.

The use of EMG to trigger ventilatory support apparatuses requires extremely high quality of the EMG signal. Filtering and artifacts due to movements of the diaphragm with respect to the muscle must be minimized. Signal artifacts of nondiaphragmatic origin must be eliminated. An example of signal artifacts of non-diaphragmatic origin is ECG.

The objects, advantages and other features of the present invention will become more apparent upon reading of the following non restrictive description of a preferred embodiment thereof, given by way of example only with reference to the accompanying drawings.

BRIEF DESCRIPTION OF THE DRAWINGS

In the appended drawings:

FIG. 10a is a graph of respiratory and expiratory flow versus time for quiet breathing of a chronic obstructive pulmonary disease (COPD) patient qui and FIG. 10b is a graph of the RMS value of EMG versus time for quiet breathing of a COPD patient, the graphs of FIGS.

10a and 10b showing the time delay from EMG to airway inspiratory flow; and

DETAILED DESCRIPTION OF THE PREFERRED EMBODIMENT

Although the preferred embodiment of the present invention will be described in relation to the use of an EMGdi signal obtained by means of a double subtracted signal and representative of the myoelectrical activity of the diaphragm, it should be kept in mind that it is within the scope of the present invention to use another type of EMGdi signal or to use a signal representative of the myoelectrical activity of muscles other than the diaphragm but associated with inspiratory effort to trigger the ventilatory support apparatus. Examples of other muscles are parasternal intercostal muscles, sternocleidomatoids, scalenes, alae nasi, etc. The myoelectrical activity of these muscles can eventually be detected by means of electrodes directly implanted in the muscle.

Also, although the preferred embodiment of the present invention will be described in relation to inspiratory support, it should be kept in mind that the present invention also applies to support of other respiration-type activity such as expiration support.

Signal Acquisition and Processing

The crural diaphragm EMG is recorded from a sheet of muscle whose fiber direction is mostly perpendicular to an esophageal bipolar electrode. The region from which the action potentials are elicited, the electrically active region of the diaphragm (DDR), and the center of this region, the DDR center, may vary during voluntary contractions, in terms of their position with respect to an esophageal electrode. Depending on the position of the bipolar electrode with respect to the DDR center, the EMGdi signal is filtered to different degrees.

Based on experimental results and anatomical descriptions of the crural diaphragm, a transfer function for diaphragm EMG measured with bipolar electrodes was developed:

$$\text{Perpendicular filtering} \approx \frac{(K_0(\omega(h-d)/v) - K_0(\omega(h+d)/v))^2}{K_0^2(\omega a/v)}$$

where, $K_0(\ )$ modified Bessel function, $\omega$=angular frequency (i.e. $2\pi f$ (f being the frequency), h=distance between the signal source and observation point, d=½ inter-electrode distance, v=conduction velocity, a=muscle fiber diameter.

Based on this transfer function, a new signal analysis procedure was developed which involves: (a) locating the electrode pair at the center of the DDR, (b) selecting the signals above and below the center of the DDR (reversed in polarity) yielding the highest signal-to-noise ratio and (c) subtracting these two signals (double subtraction technique). The double subtraction technique reduces the influence of movement of the DDR center relative to the electrode array on the EMG power spectrum center frequency and root mean square values, increases the signal to noise ratio by 2 dB, and increases the number of EMG samples that are accepted by the signal quality indices by 50%. A more detailed description of the above mentioned double subtraction technique is given hereinbelow.

Figure 1:
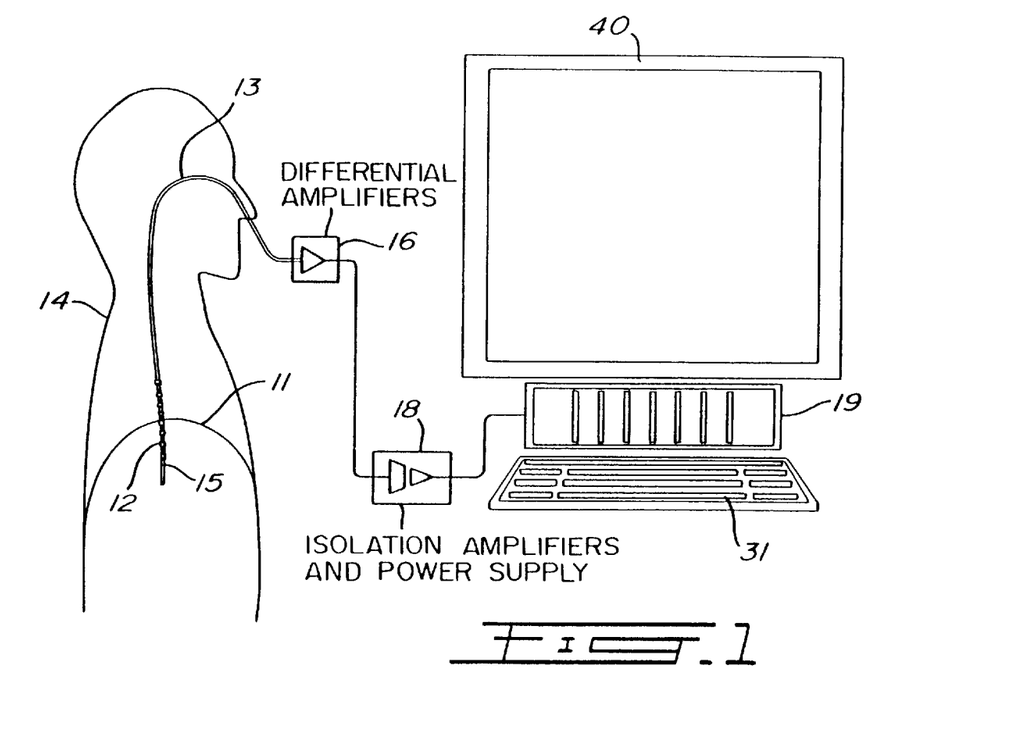
FIG. 1 is a schematic representation of a set-up of an EMG analysis system.
Figure 2:
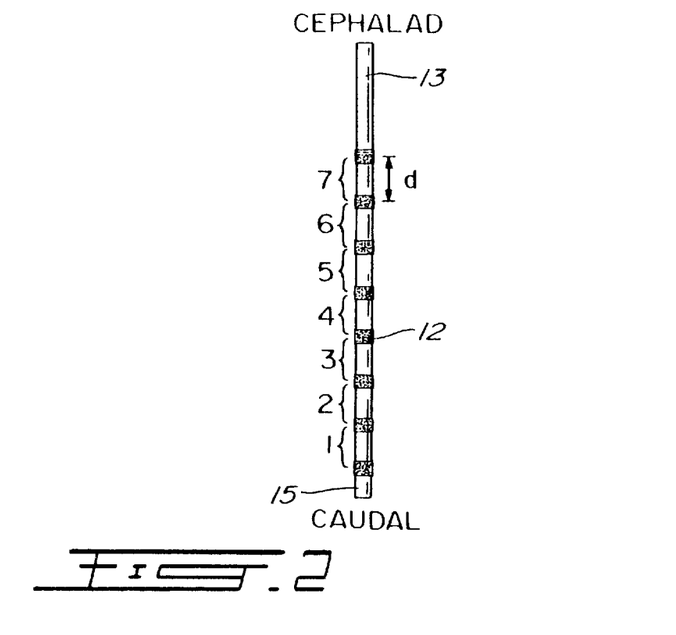
FIG. 2 is a section of oesophageal catheter on which an array of electrodes of the EMG analysis system of FIG. 1 is mounted.

For example, to measure EMG activity of the diaphragm 11 (EMGdi) of a human patient 14, an array of electrodes such as 12 (FIGS. 1 and 2) are mounted on the free end section 15 of an oesophageal catheter 13, with a constant inter-electrode distance d (FIG. 2). As shown in FIG. 1, the catheter 13 is introduced into the patient's oeaophagus through one nostril or the mouth until the array of electrodes 12 is situated at the level of the gastroesophageal junction. The diaphragm 11 and/or the oesophagus slightly moves during breathing of the patient 14 whereby the array of electrodes 12 also slightly moves about the diaphragm 11. As will be explained in the following description, automatic compensation for this displacement is provided for.

According to a preferred embodiment, an electrode 12 is mounted on the free end section 15 of the catheter 13 by winding stainless steel wire (not shown) around that catheter 13. The wound stainless steel wire presents a rough surface smoothed out by solder, which in turn is electroplated with nickel, copper and then gold or silver. Of course, it is within the scope of the present invention to use other electrode structures. Also, the electrodes 12 can possibly be applied to a nasogastric feeding tube (not shown) which is routinely introduced in intensive-care unit (ICU) patients.

Electric wires (not shown) interconnect each pair of successive electrodes such as 1–7 (FIG. 2) with a respective one of a group of differential amplifiers 16. Obviously, these electric wires follow the catheter 13 from the respective electrodes 12 to the corresponding amplifiers 16, and are preferably integrated to the catheter 13. Preferably, the electric wires transmitting the EMGdi signals collected by the various pairs 1–7 of electrodes 12 are shielded to reduce the influence of external noise, in particular disturbance from the 50 or 60 Hz current and voltage of the electrical mains.

The group of differential amplifiers 16 amplifies (first subtraction step of the double subtraction technique) and band-pass filters each EMGdi signal. This first subtraction step may also be carried out in the personal computer 19 when the amplifiers 16 are single-ended or equivalently designed amplifiers (monopolar readings).

Figure 3:
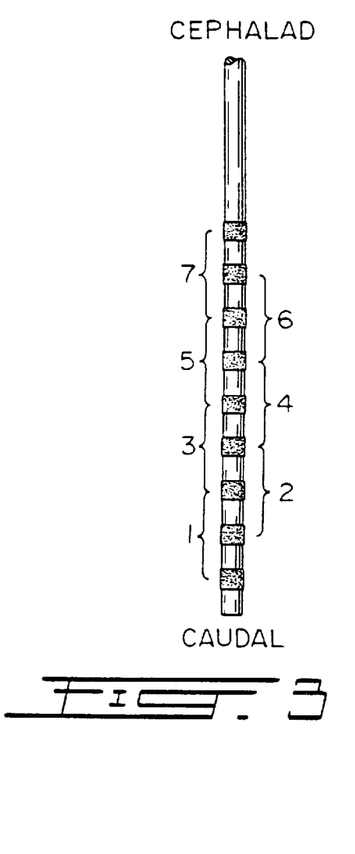
FIG. 3 illustrates a section of oesophageal catheter on which a second embodiment of the array of electrodes is mounted.

In the example illustrated in FIGS. 1 and 2, the free end section 15 of the catheter 13 is provided with an array of eight electrodes 12 defining seven pairs 1, 2, 3, 4, 5, 6 and 7 of successive electrodes 12 respectively collecting seven different EMGdi signals. Although it has been found that EMG activity of the diaphragm (EMGdi) can be measured accurately with an oesophageal catheter 13 provided on the free end section 16 thereof with an array of eight electrodes 12, a different number and/or configuration of pairs of electrodes 12 can be contemplated depending on the patient's anatomy and movement of the diaphragm. Also, the pairs 1–7 do not need to be pairs of successive electrodes; FIG. 3 illustrates an array of nine electrodes to form seven overlapping pairs of electrodes 1–7.

A major problem in recording EMGdi signals is to maintain the noise level as low and as constant as possible. Since the electric wires transmitting the EMGdi signals from the electrodes 12 to the differential amplifiers 16 act as an antenna, it is crucial, as indicated in the foregoing description, to shield these electric wires to thereby protect the EMGdi signals from additional artifactual noise. Also, the package enclosing the differential amplifiers 16 is preferably made as small as possible (miniaturized) and is positioned in close proximity to the patient's nose to decrease as much as possible the distance between the electrodes 12 and the amplifiers 16.

The amplified EMGdi signals are sampled by a personal computer 19 through respective isolation amplifiers of a unit 18, to form signal segments of fixed duration. Unit 18 supplies electric power to the various electronic components of the differential and isolation amplifiers while ensuring adequate isolation of the patient's body from such power supply. The unit 18 also incorporates bandpass filters included in the respective EMGdi signal channels to eliminate the effects of aliasing. The successive EMGdi signal segments are then digitally processed into the personal computer 19 after analog-to-digital conversion thereof. This analog-to-digital conversion is conveniently carried out by an analog-to-digital converter implemented in the personal computer 19. The personal computer 19 includes a monitor 40 and a keyboard 31.

It is believed to be within the capacity of those of ordinary skill in the art to construct suitable differential amplifiers 16 and an adequate isolation amplifiers and power supply unit 18. Accordingly, the amplifiers 16 and the unit 18 will not be further described in the present specification.

Figure 4:
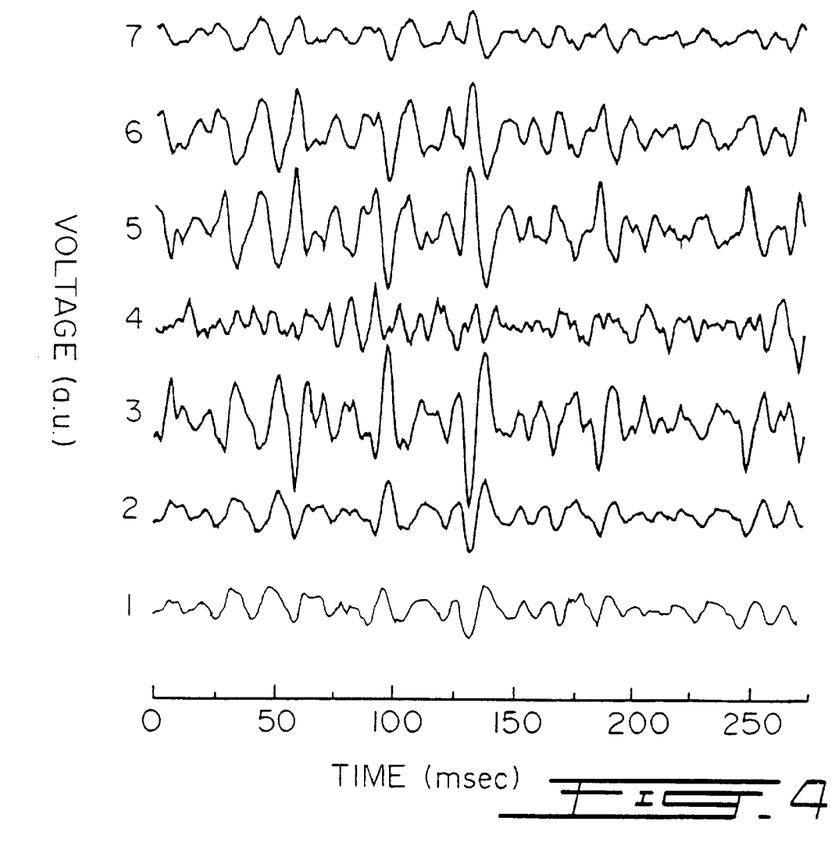
FIG. 4 is a graph showing a set of EMG signals of the diaphragm (EMGdi signals) detected by pairs of successive electrodes of the array of FIG. 2.

An example of the seven EMGdi signal components (hereinafter EMGdi signals) collected by the pairs 1–7 of successive electrodes 12 (FIGS. 1 and 2) and supplied to the computer 19 is illustrated in FIG. 4.

Figure 6A:
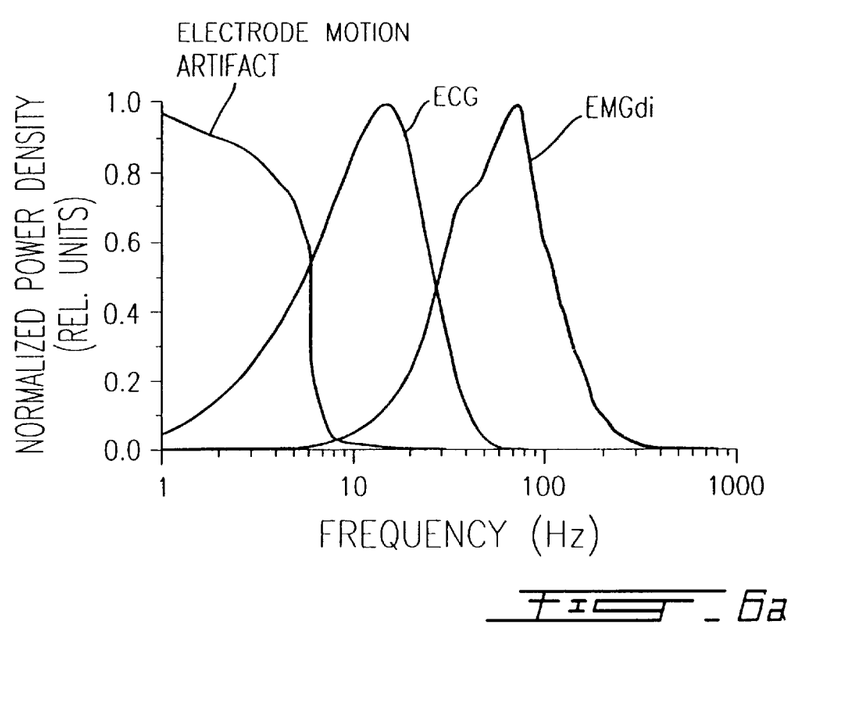
FIG. 6a is a graph showing the power density spectrum of electrode motion artifacts, the power density spectrum of ECG, and the power density spectrum of EMGdi signals.

The first operation (step 501) performed by the computer 19 is a filtering operation to remove from all the EMGdi signals of FIG. 4 electrode motion artifacts, ECG, 50 and 60 Hz interference from the electrical network, and high frequency noise. The graph of FIG. 6a shows the power density spectrum of the above defined electrode motion artifacts, the power density spectrum of ECG, and the power density spectrum of EMGdi signals. Just a word to mention that motion artifacts are induced by motion of the electrodes 12. More generally, motion artifacts are defined as a low frequency fluctuation of the EMGdi signals' DC level induced by mechanical alterations of the electrode metal to electrolyte interface i.e. changes in electrode contact area and/or changes in pressure that the tissue exerts on the electrode.

Figure 6B:
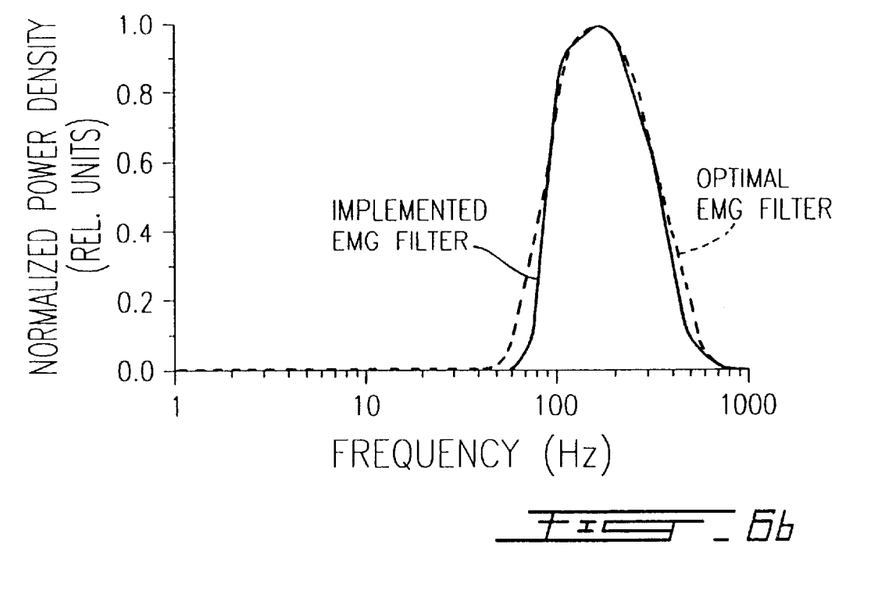
FIG. 6b is a graph showing an example of transfer function for a filter to be used for filtering out the electrode motion artifacts, ECG, the 50 or 60 Hz disturbance from electrical mains and high frequency noise.

The influence of ECG on the EMGdi signals can be suppressed or eliminated in different ways. Depending on the working mode, i.e. on-line or off-line analysis time domain or frequency domain processing different optimal signal conditioning methods can be chosen. In time critical applications, an optimized filtering might be a reasonable choice. FIG. 6b presents an optimal filter transfer function to isolate the diaphragm EMG from a compound signal including ECG and also disturbed by background noise and electrode motion artifacts. In FIG. 6b, the dashed line shows the optimal transfer function, and the solid line the transfer function implemented by the inventors. FIG. 6b is therefore an example of filter transfer function that can be used in step 501 for filtering out the electrode motion artifacts, ECG, the 50 or 60 Hz disturbance from the electrical mains, and the high frequency noise. Processing of the EMGdi signals by the computer 19 to follow as closely as possible the optimal transfer function of FIG. 6b will conduct adequately filtering step 501.

Figure 10A:
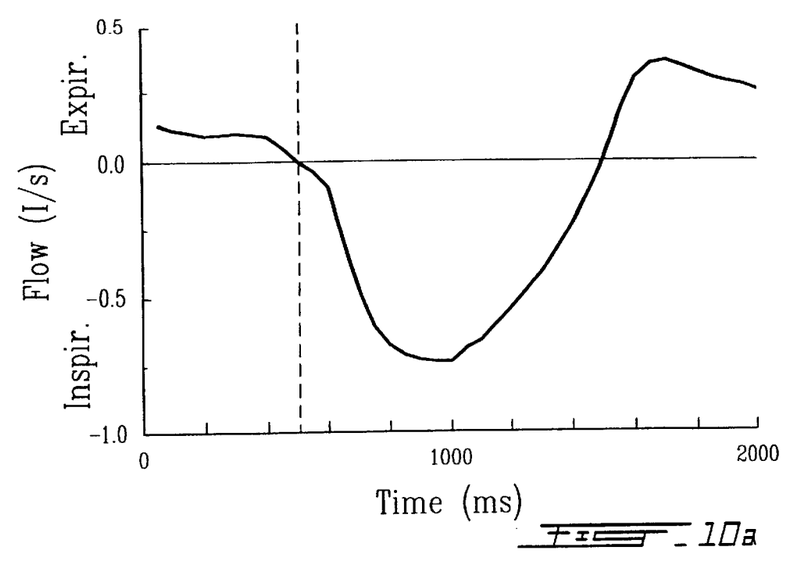
Figure 10B:
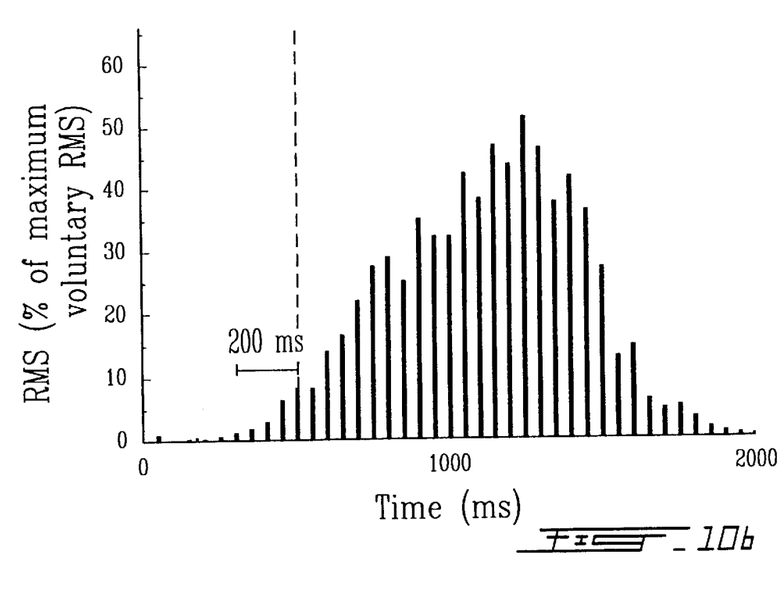

An example of integrated EMGdi signal from a COPD patient in relation to esophageal and gastric pressure is depicted in FIGS. 10a and 10b.

Determination of the Position of the Center of the DDR (Step 502)

As the diaphragm is generally perpendicular to the longitudinal axis of the oesophageal catheter 13 equipped with an array of electrodes 12, only a portion of the electrodes 12 are situated in the vicinity of the diaphragm. It is therefore important to determine the position of the diaphragm with respect to the oesophageal electrode array.

The portion of the crural diaphragm 11 which forms the muscular tunnel through which the oesophageal catheter 13 is passed is referred to the "diaphragm depolarizing region" (DDR). The thickness of the DDR is 20–30 mm. It can be assumed that, within the DDR, the distribution of active muscle fibers has a center from which the majority of the EMGdi signals originate, i.e. the "diaphragm depolarizing region center" (DDR center). Therefore, EMGdi signals detected on opposite sides of the DDR center will be reversed in polarity with no phase shift; in other words, EMGdi signals obtained along the electrode array are reversing in polarity at the DDR center.

Moving centrally from the boundaries of the DDR, EMGdi power spectrums progressively attenuate and enhance in frequency. Reversal of signal polarity on either aide of the electrode pair 4 with the most attenuated power spectrum confirms the position from which the EMGdi signals originate, the DDR center.

Figure 5A:
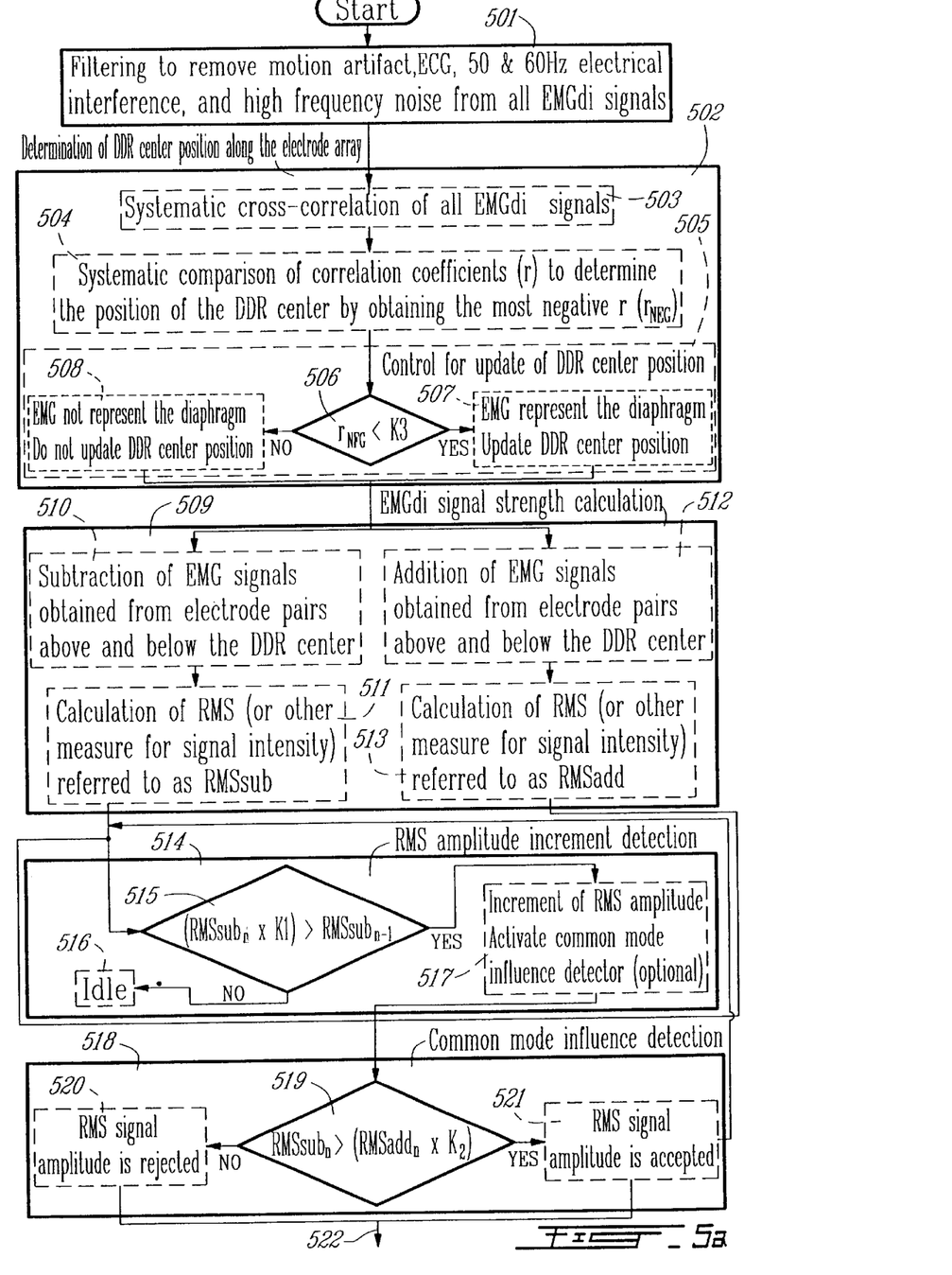
FIG. 5a is a first portion of a flow chart illustrating a preferred embodiment of the method and device according to the invention for triggering ventilatory support in response to myoelectrical activity of a respiration-related muscle, for example the diaphragm.
Figure 5B:
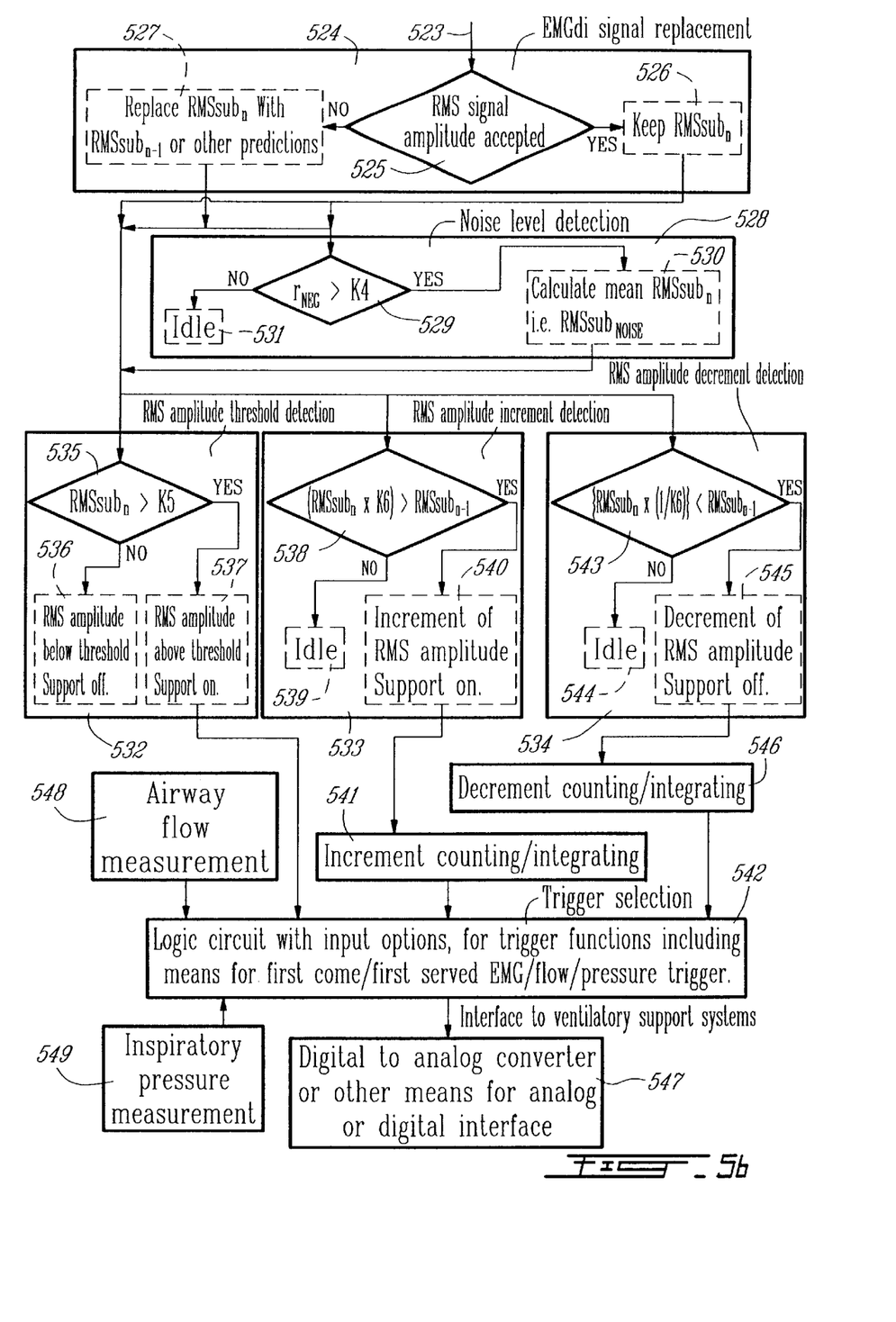
FIG. 5b is a second portion of the flow chart illustrating a preferred embodiment of the method and device according to the invention for triggering ventilatory support in response to myoelectrical activity of the respiration-related muscle, for example the diaphragm.

In step 502 of FIG. 5a, the position of the center of the DDR along the array of electrodes 12 is determined. Referring to FIG. 5, the first task of the computer 19 is to determine the position of the center of the DDR along the array of electrodes 12. The center of the DDR is repeatedly updated, that is re-determined at predetermined time intervals.

For that purpose, the EMGdi signals are cross-correlated in pairs in substep 503 to calculate cross-correlation coefficients r. As well known to those of ordinary skill in the art, cross-correlation is a statistical determination of the phase relationship between two signals and essentially calculates the similarity between two signals in terms of a correlation coefficient r. A negative correlation coefficient r indicates that the cross-correlated signals are of opposite polarities.

Figure 7:
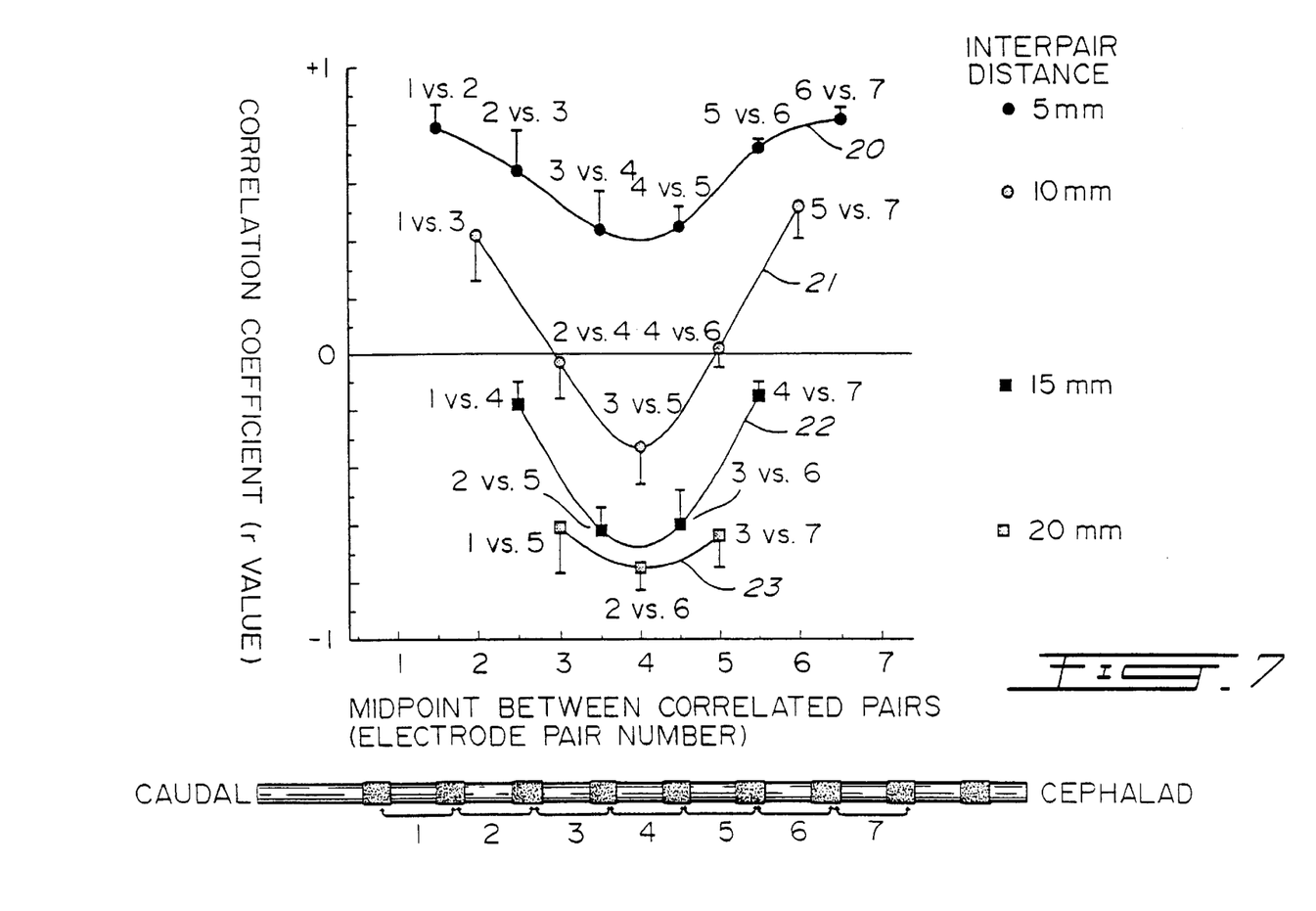
FIG. 7 is a graph showing the distribution of correlation coefficients calculated for determining the position of the center of the depolarizing region of the respiration-related muscle, for example the diaphragm along the array of electrodes of FIG. 2.

FIG. 7 shows curves of the value of the correlation coefficient r versus the midpoint between the pairs of electrodes from which the correlated EMGdi signals originate. In this example, the interelectrode distance is 10 mm. Curves are drawn for distances between the correlated pairs of electrodes 12 of 5 mm (curve 20), 10 mm (curve 21), 15 mm (curve 22) and 20 mm (curve 23). One can appreciate from FIG. 7 that negative correlation coefficients r are obtained when EMGdi signals from respective electrode pairs situated on opposite sides of the electrode pair 4 are cross-correlated. It therefore appears that the change in polarity occurs in the region of electrode pair 4, which is confirmed by the curves of FIG. 4. Accordingly, it can he assumed that the center of the DDR is situated substantially midway between the electrodes 12 forming pair 4.

In substep 504, the correlation coefficients are systematically compared to determine the center of the DDR. For example, the center of the DDR can be precisely determined by interpolation using a square law based fit of the three most negative correlation coefficients of curve 21 obtained by successive cross-correlation of the EMGdi signal segments from each electrode pair to the EMGdi signal segments from the second next electrode pair. Association of the center of the DDR to a pair of electrodes 12 provides a "reference position" from which to obtain EMGdi signal segments within the DDR.

As mentioned in the foregoing description, the position of the DDR center along the array of electrodes 12 is continuously updated, i.e. re-calculated at predetermined time intervals overlapping or not. In substep 505, update of the position of the DDR center is controlled by comparing the most negative correlation coefficient $r_{NEG}$ to a constant $K_3$ (substep 506). If $r_{NEG} < K_3$, it is considered that the EMGdi signal represents the diaphragm and the position of the center of the DDR is updated (substep 507); if $r_{NEG}>K_3$, it is considered that the EMGdi signal does not represent the diaphragm and the position of the center of the DDR is not updated (substep 508). The control carried out in substep 505 is essential in overcoming the artifactual influence on the EMGdi power spectrum or signal strength measurement.

It has been experimentally demonstrated that EMGdi signals recorded in the oesophagus of adults are satisfactory as long as they are obtained from electrode pairs (with an inter-electrode distance situated between 5 and 20 mm) positioned at a distance situated between 5 and 30 mm on the opposite sides of the DDR center (the inter-pair distance being therefore situated between 5 and 30 mm). With infants, this may change. Although EMGdi signals obtained from these positions offers a clear improvement in acceptance rate, the signal-to-noise ratio during quiet breathing still tends to remain unsatisfactorily low.

Figure 8:
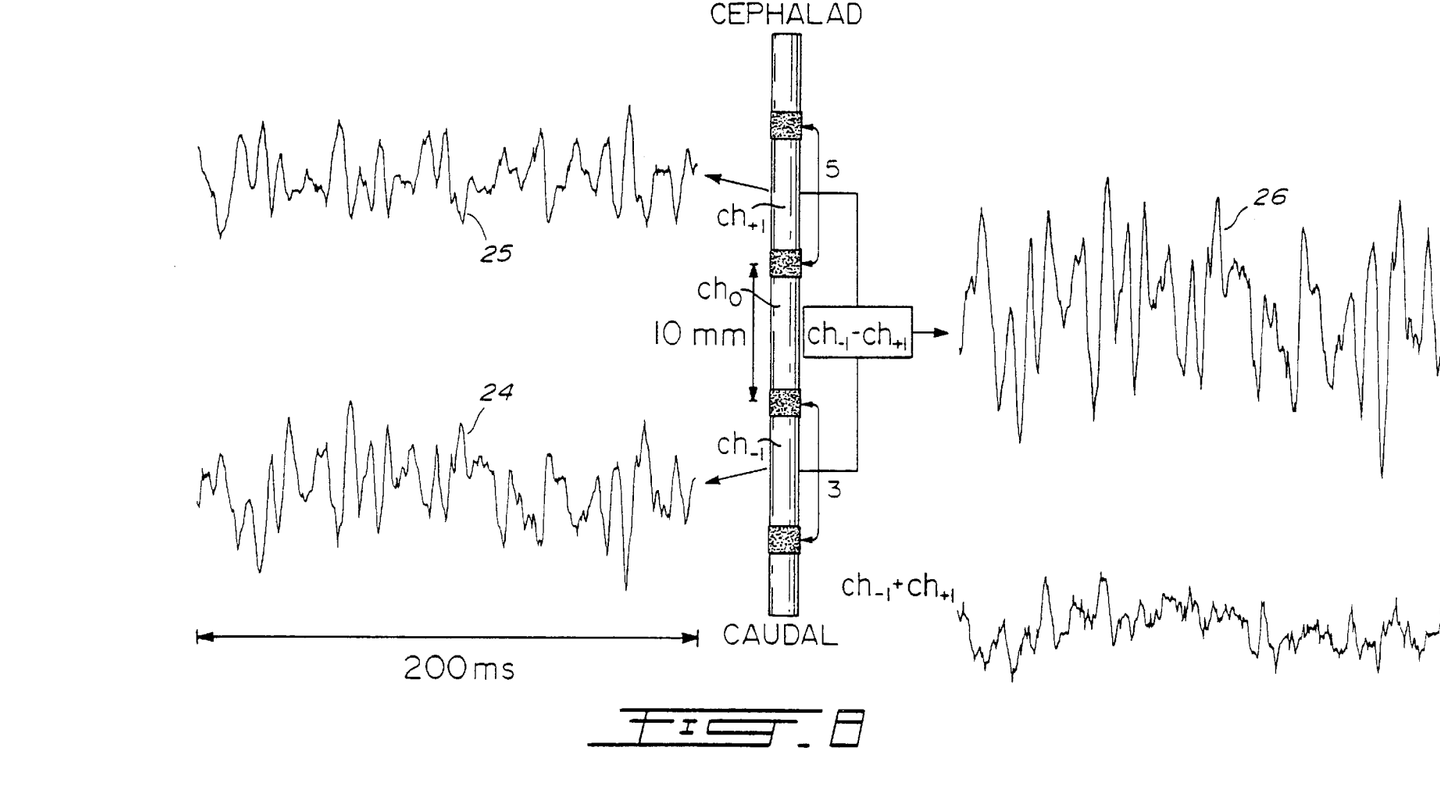
FIG. 8 is a schematic diagram illustrating in the time domain a double subtraction technique for improving the signal-to-noise ratio and to reduce an electrode-position-induced filter effect.

For example, in FIG. 4, the EMGdi signals originating from the electrode pairs 3 and 5 situated respectively 10 mm below and 10 mm above the DDR are strongly inversely correlated at zero time delay. In contrast to the inversely correlated EMGdi signals, the noise components for electrode pairs 3 and 5 are likely to be positively correlated. Hence, as illustrated in FIG. 8, subtraction of the EMGdi signals 24 and 25 from electrode pairs 3 and 5 will result into an addition of the corresponding EMGdi signals (see signal 26) and into a subtraction, that is an elimination of the common noise components. This technique is referred to as "the double subtraction technique".

This second subtraction step of the double subtraction technique can be carried out either in the time domain, or after conversion of signals 24 and 25 into the frequency domain. Double subtraction technique can be performed by subtracting other combinations of signals, or by altering the polarities of electrode pairs. What is important is to subtract two signals of opposite polarities obtained in the vicinity of the muscle on opposite sides of the DDR, or if polarity is altered on opposite sides of the DDR to add signals from opposite sides of the DDR.

Therefore, double-subtracted signal segments 509 are obtained at the output of step 510 by subtracting the EMGdi signal segments from the pair of electrodes 12 in optimal location above the diaphragm from the EMGdi signal segments from the pair of electrodes 12 in optimal location below the diaphragm.

Figure 9:
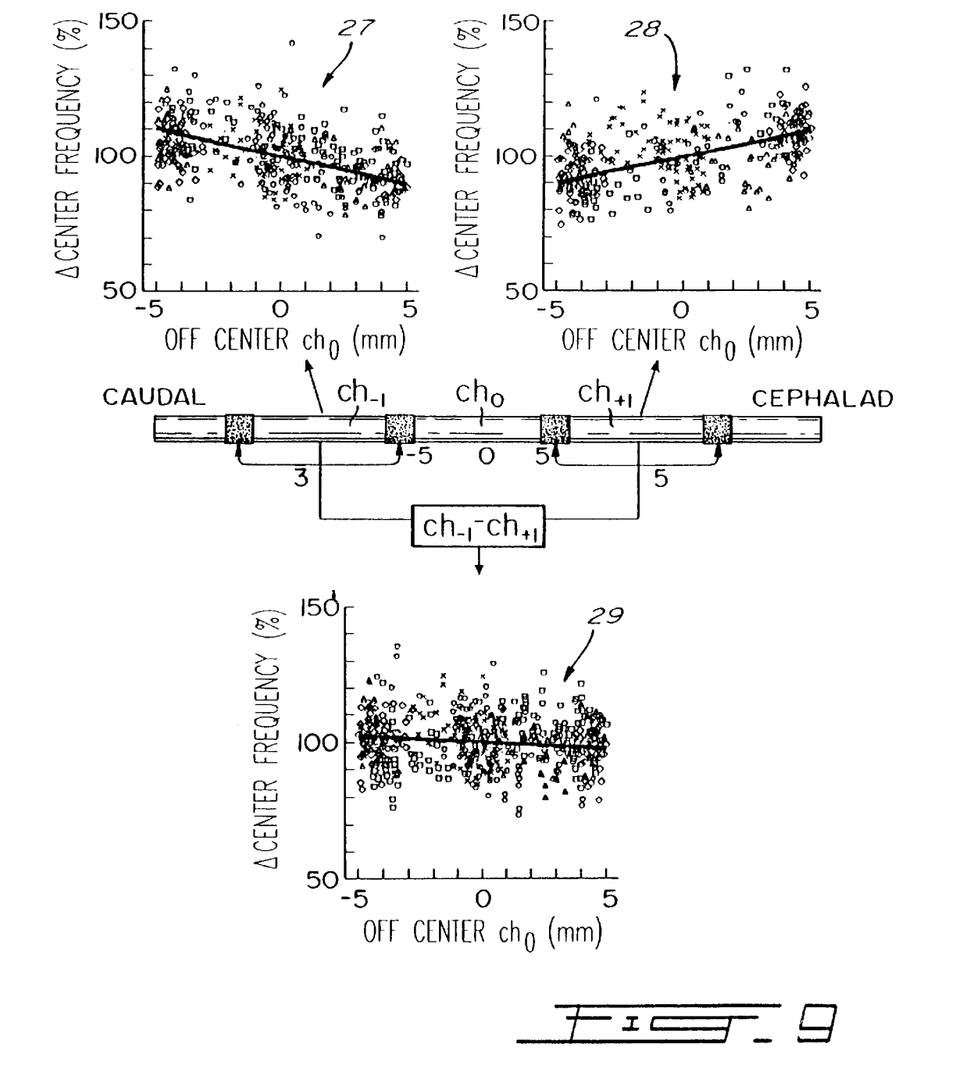
FIG. 9 is a schematic diagram illustrating in the frequency domain stabilization by the double subtraction technique of the center frequency upon displacement of the center of the depolarizing region of the respiration-related muscle, for example the diaphragm along the array of electrodes of FIG. 2.

The double subtraction technique compensates for the changes in signal strength and frequency caused by movement of the diaphragm 11 (FIG. 1) and/or the oesophagus during breathing of the patient 14 causing movement of the array of electrodes 12 with respect to the diaphragm 11. Referring to FIG. 9, off center of the array of electrodes 12 (electrode-position-induced filter effect) causes a variation of center frequency values (see curves 27 and 28) for the EMGdi signals from the electrode pairs 3 and 5. The double subtraction technique eliminates such variation of center frequency values as indicated by curve 29 as well as variation of signal strength. Therefore, the reciprocal influence of the position of the DDR center on the EMGdi signal frequency content is eliminated by the double subtraction technique.

It has been found that the double subtraction technique may improve the signal-to-noise ratio by more than 2 dB and reduce an electrode-position-induced filter effect. Double subtraction technique is also responsible for a relative increase in acceptance rate by more than 50%.

Cross-talk signals from adjacent muscles are strongly correlated at zero time delay and equal in polarity between all pairs of electrodes 12. Hence, these cross-talk signals appear as a common mode signal for all electrode pairs and therefore, are eliminated by the double subtraction technique.

EMG Signal Strength Calculation (Step 509)

In step 509, the strength of the EMGdi signal is calculated. In a first substep 510, a pair of EMGdi signals (see signal 1–7 of FIG. 4) obtained from electrode pairs above and below the DDR center are subtracted from each other and the RMS (Root-Mean-Square) value of the resulting signal is calculated and referred to as RMSsub (substep 511). Measures of signal intensity other than the RMS value can also potentially be used.

In a substep 512, the above mentioned pair of EMGdi signals (see signal 1–7 of FIG. 4) obtained from electrode pairs above and below the DDR center are added to each other and the RMS (Root-Mean-Square) value of the resulting addition signal is calculated and referred to as RMSadd (substep 513). Measures of signal intensity other than the RMS value can also potentially be used.

Detection of an Increment of the RMS Signal Amplitude (Step 514)

In step 514, a sufficient increment of the RMS signal amplitude RMSsub is detected. More specifically, in substep 515, the RMS amplitude $RMSsub_n$ of the last EMGdi subtraction signal segment as calculated by substep 511 is compared with the $RMSsub_{n-1}$ of EMGdi subtraction signal segment last accepted in substep 521. If ($RMSsub_n$ x $K_1$)<$RMSsub_{n-1}$, no increment is detected and the device will wait until analysis of the next EMGdi subtraction signal segment is performed. On the contrary, if ($RMSsub_n$ x $K_1$)>$RMSsub_{n-1}$, an increment of the RMS intensity of the EMGdi signal is detected and detection of the common mode influence (step 518) is activated. Of course, the multiplication operation (x $K_1$) can be replaced by any other suitable mathematical operation conducted on either the term $RMSsub_n$ or $RMSsub_{n-1}$.

Detection of Common Mode Influence (Step 618)

Step 518 enables detection of signal artifacts of non-diaphragmatic origin. As indicated in the foregoing description, EMGdi signals generated by the diaphragm and recorded on either side of the diaphragm will have reversed polarity and no time delay. Accordingly, a subtraction signal representative of the difference between these two EMGdi signals will have a larger amplitude than an addition signals representing the sum of such EMGdi signals. In contrast, signals generated away from and on the same side of the diaphragm will have the same polarity on all electrode pairs and no time delay. Also signals from the heart that are not obtained with electrode pairs located too far apart will have similar shape but with a time delay. Different from signals with reversed polarity, subtracted signals with same polarity will have smaller amplitudes than added signals. Hence the ratio or difference between sum and difference between signals obtained from the same electrode pairs on either side of the diaphragm can indicate if a signal is of diaphragm or artifactual origin.

For that purpose in substep 519, the amplitude $RMSsub_n$ is compared with the amplitude $RMSadd_n$ multiplied by a constant $K_2$. Just a word to recall that the indicia "n" is representative of the last EMGdi subtraction or addition signal segment. If $RMSsub_n<(RMSadd_n$ x $K_2)$, the RMS signal amplitude is rejected (substep 520) and the two EMGdi signals are considered to have an artifactual origin. If $RMSsub_n>(RMSadd_n$ x $K_2)$, the RMS signal amplitude is accepted (substep 521) and the two EMGdi signals are considered to have a diaphragm origin. Of course, the multiplication operation (x $K_2$) can be replaced by any other suitable mathematical operation conducted on either the term $RMSsub_n$ or $RMSadd_n$.

Replacement of EMGdi Signal

The output 522 of the substeps 520 and 521 is connected to the input 523 of the substep 525. In EMGdi signal replacement step 524, a substep 525 determines whether the last RMS signal amplitude is accepted. If the last RMS signal amplitude is accepted, $RMSsub_n$ is kept (substep 526). If the last RMS signal amplitude is not accepted, $RMSsub_n$ is replaced by $RMSsub_{n-1}$ or with another prediction (substep 527).

Noise Level Detection (Step 528)

An increase in amplitude of $RMSsub_n$ does not necessarily mean that the diaphragm is the signal source. It is therefore required to discriminate signals originating from the diaphragm from signals of other origins. In the foregoing description, it has been described that a technique of sequential cross-correlation of the EMGdi signals from pairs of electrodes 12 can be used to determine the location of the diaphragm by the most negative correlation coefficient $r_{NEG}$. Any simplified calculation of correlation can be used. The magnitude of the correlation coefficient $r_{NEG}$ is characteristic for each subject but is typically negative when the diaphragm is active. If the diaphragm is not active, the negative correlation coefficient $r_{NEG}$ is very low or the correlation coefficient is positive. The onset of diaphragm activation can therefore be detected through the amplitude of the correlation coefficient $r_{NEG}$.

An alternative to step 528 is to detect the onset of inspiration through detection of airway inspiratory flow.

To determine the mean level of noise $RMSsub_{NOISE}$ (step 528), a mean amplitude of $RMSsub_n$ is calculated. For that purpose, when $r_{NEG}>K_4$, $K_4$ being a constant, this indicates that the diaphragm is not active (substep 529) and the mean level of $RMSsub_n$, i.e. $RMSsub_{NOISE}$ is calculated (substep 530) and supplied to step 532. If $R_{NEG}<K_4$, step 528 remains in an idle state (step 531).

Steps 532, 533 and 534 is a possible method for triggering ventilatory support systems from EMGdi signal measurements. Any increase in EMGdi signal amplitude, it's integrals or derivatives or combinations thereof, detected via an EMG recording of the diaphragm or other muscles associated with inspiration above a desired threshold level and exceeding a desired duration can be used to indicate the onset of an inspiratory effort. The measurement of inspiratory EMG can be obtained with any device placed in the vicinity of the inspiratory muscle, inserted or implanted on the surface of or into the muscle of interest. Determination of the trigger level to be exceeded in terms of amplitude and duration can either be performed by manual adjustment supervised via visual feedback, or automatically by letting the trigger level be relative to the above described mean noise level. An algorithm can further be used to trigger the ventilatory support system when the amplitude of a EMG signal segment of defined duration exceeds the threshold, The duration that the EMG amplitude remains above the threshold level can be used to decide the duration of the breath e.g. the ventilatory support system can start and deliver a full breath independent of the presence of EMG activity that exceeds the threshold level. The algorithm can also be adjusted to discontinue the ventilatory support if the EMG Amplitude drops below the threshold level, or in response to a decrease in amplitude that exceeds a given magnitude (decrement).

RMS Amplitude Threshold Detection (Step 632)

In substep 535, if $RMSsub_n<K_5$ the RMS amplitude is below the threshold and the ventilatory support system is not triggered (substep 536). Therefore, no ventilatory support is provided to the patient. $K_5$ is a constant equal to $RMSsub_{NOISE}$ x $K_7$, $K_7$ being another constant. This will prevent the ventilatory support system from being triggered in the eventuality that the diaphragm is not active, i.e. in the case in which $r_{NEG}>K_4$ (substep 529). Again, the multiplication operation (x $K_7$) can be replaced by any other suitable mathematical operation conducted on term $RMSsub_{NOISE}$.

In substep 535, if $RMSsub_n>K_5$ the RMS amplitude is higher than the threshold and triggering of the ventilatory support system is requested (substep 537) to provide ventilatory support to the patient. Otherwise, no ventilatory support is provided (substep 536).

RMS Amplitude Increment Detection (Step 533)

In substep 538, $RMSsub_{n-1}$ is compared to ($RMSsub_n$ x $K_8$). If ($RMSsub_n$ x $K_8$)<$RMSsub_{n-1}$, step 533 remains in an idle state (substep 539) and no ventilatory support to the patient is requested. If ($RMSsub_n$ x $K_8$)>$RMSsub_{n-1}$, this indicates an increment of the RMS amplitude and triggering of the ventilatory support system is requested through an increment counting/integrating step 541 to support the patient substep 540). The multiplication operation (x $K_6$) can be replaced by any other suitable mathematical operation conducted on either the term $RMSsub_n$ or $RMSsub_{n-1}$.

The function of the increment counting/integrating step 541 is to determine the time/magnitude response. Step 541 averages the increment signal to adjust sensitivity.

RMS Amplitude Decrement Detection (Step 534)

In substep 543, $RMSsub_{n-1}$ is compared to ($RMSsub_n$ x (1/$K_6$)). If ($RMSsub_n$ x (1/$K_6$))>$RMSsub_{n-1}$, step 534 remains in an idle state (substep 544) and no ventilatory support to the patient is requested. If ($RMSsub_n$ x (1/$K_6$)) <$RMSsub_{n-1}$, this indicates a decrement of the RMS amplitude and non-triggering of the ventilatory support system is requested through a decrement counting/integrating step 546 (substep 545). Of course, the multiplication operation (x (1/$K_8$)) can be replaced by any other suitable mathematical operation conducted on either the term $RMSsub_n$ and $RMSsub_{n-1}$.

The function of the decrement counting/integrating step 546 is to determine the time/magnitude response. Step 546 averages the decrement signal to adjust sensitivity.

Trigger Selection Stop 542

Step 542 is responsive to EMG (signals from substeps 537, 541 and 546), airway inspiratory flow (step 548) and/or pressure (step 549) for triggering a ventilatory support system (ventilator) through an interface 547. The interface 547 may comprise a digital-to-analog converter and/or other means for analog and digital interface.

More specifically, step 542 is a method for triggering a ventilatory support system with combined use of EMG, airway inspiratory flow and/or pressure. The decision for triggering will be made by a logic circuit on a "first come, first served" basis. For example, if the diaphragm EMG (or EMG of any other inspiratory related muscle) indicates an inspiratory effort before airway inspiratory flow and/or pressure indicate the onset of inspiration, the ventilatory support will be engaged. In the same fashion, the ventilatory support will be initiated if the inspiratory effort is detected by a threshold for airway inspiratory flow and/or pressure being exceeded before the EMG threshold is exceeded.

Any change in airway inspiratory flow and/or pressure, its integrals or derivatives or combinations thereof, in the inspiratory direction beyond a desired threshold level and detected via the inspiratory and/or expiratory lines can be used to indicate the onset of an inspiration.

Figure 11A:
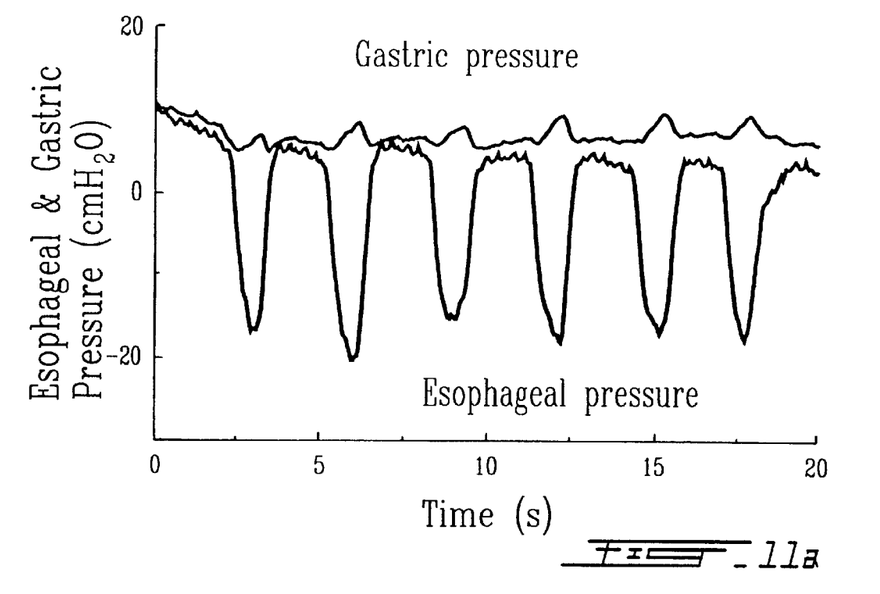
FIG. 11a is a graph of esophageal and gastric pressure versus time for quiet breathing of a chronic obstructive pulmonary disease (COPD) patient and FIG. 11b is a graph of the RMS value of EMG versus time for quiet breathing of a COPD patient, the graphs of FIGS. 11a and 11b showing the relation between EMG and the esophageal and gastric pressure.
Figure 11B:
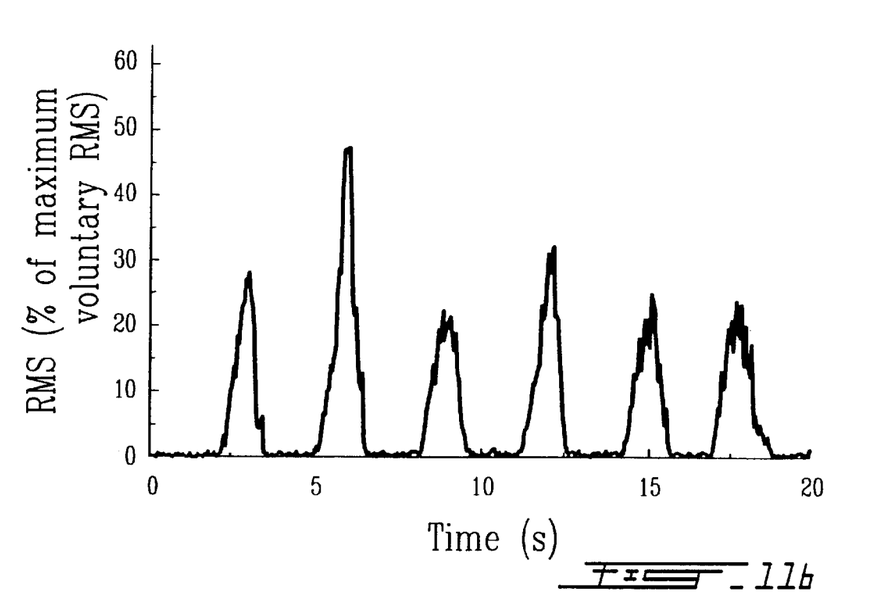

The graphs of FIGS. 10a and 10b show, in the case of quiet breathing of a COPD patient that EMG RMS signal will be detected approximately 200 ms prior to the onset of airway inspiratory flow. The graphs of FIGS. 11a and 11b show, still in the case of quiet breathing of a COPD patient, a similar relation between EMG RMS signal and the gastric and esophageal pressure. In this particular example, triggering in response to EMG will enable the lung ventilator to assist the patient directly at the onset of inspiration occuring 200 ms after detection of EMG RMS amplitude signal.

The method and device according to the invention is applicable in all patients (adults and infants) on ventilatory support and will enhance the possibilities to obtain spontaneous breathing and optimize patient ventilator interaction. The method and device apply to all kinds of ventilatory support systems used in intensive care unit settings or other wards where assisted ventilation is applied.

Finally, it should be kept in mind that:
the EMG can be measured not only on the diaphragm but on any other inspiratory related muscle, obtained with the double subtraction technique or not;
steps 502 and 518 of FIG. 5a are exclusively used with the double subtraction technique;
common mode influence detection step 518 is optional;
step 528 is optional;
the operation of the device according to the invention can be based either on the amplitude of the signals or the area under the curve (integration) of these signals, or any other measure of signal strength.

Although the present invention has been described hereinabove with reference to preferred embodiments thereof, these embodiments can be modified at will, within the scope of the appended claims, without departing from the spirit and nature of the subject invention.

What is claimed is:

1. A method for triggering ventilatory support from a ventilatory apparatus connected to a patient's respiratory system to assist respiration of said patient, comprising:
sensing myoelectrical activity of a respiratory-related muscle of the patient, to thereby detect respiratory effort of said patient;
in response to the sensed muscle myoelectrical activity, calculating a real-time myoelectrical signal representative of a level or change in respiratory effort; and
activating/deactivating ventilatory support in relation to the myoelectrical signal to synchronise, in real-time, activating/deactivating of the ventilatory support to the patient with respiratory effort of said patient, said activating/deactivating of ventilatory support comprising:
comparing an amplitude, integral, derivative or combination thereof related to the myoelectrical signal to a given threshold; and
activating ventilatory support when said amplitude, integral, derivative or combination thereof is higher than said given threshold.

2. A method for triggering ventilatory support as recited in claim 1, further comprising filtering from the myoelectrical signal at least one of the following disturbances: motion artifacts, ECG, electrical interference, and high frequency noise.

3. A method for triggering ventilatory support from a ventilatory apparatus connected to a patient's respiratory system to assist respiration of said patient, comprising:
sensing myoelectrical activity of a respiratory-related muscle of the patient, to thereby detect respiratory effort of said patient;
in response to the sensed muscle myoelectrical activity, calculating a real-time myoelectrical signal representative of a level or change in respiratory effort; and
activating/deactivating ventilatory support in relation to the myoelectrical signal to synchronise, in real-time, activating/deactivating of the ventilatory support to the patient with respiratory effort of said patient, wherein activating/deactivating of ventilatory support comprises:
detecting an increment of an amplitude, integral, derivative or combination thereof related to the myoelectrical signal; and
activating ventilatory support in response to detection of said increment.

4. A method for triggering ventilatory support as recited in claim 3, wherein the increment detection comprises:
multiplying a current sample of the myoelectrical signal by a predetermined constant to produce a multiplied sample;
comparing the multiplied sample to a preceding sample; of the myoelectrical signal; and
detecting said increment when the amplitude, integral, derivative or combination thereof related to the multiplied sample is higher than the amplitude, integral, derivative or combination thereof related to the preceding sample.

5. A method for triggering ventilatory support from a ventilatory apparatus connected to a patient's respiratory system to assist respiration of said patient, comprising:
sensing myoelectrical activity of a respiratory-related muscle of the patient, to thereby detect respiratory effort of said patient;
in response to the sensed muscle myoelectrical activity, calculating a real-time myoelectrical signal representative of a level or change in respiratory effort; and
activating/deactivating ventilatory support in relation to the myoelectrical signal to synchronise, in real-time, activating/deactivating of the ventilatory support to the patient with respiratory effort of said patient, wherein activating/deactivating of ventilatory support comprises:
comparing an amplitude, integral, derivative or combination thereof related to the myoelectrical signal to a given threshold; and
deactivating ventilatory support when said amplitude, integral, derivative or combination thereof is lower than said given threshold.

6. A method for triggering ventilatory support from a ventilatory apparatus connected to a patient's respiratory system to assist respiration of said patient, comprising:
sensing myoelectrical activity of a respiratory-related muscle of the patient, to thereby detect respiratory effort of said patient;
in response to the sensed muscle myoelectrical activity, calculating a real-time myoelectrical signal representative of a level or change in respiratory effort; and
activating/deactivating ventilatory support in relation to the myoelectrical signal to synchronise, in real-time, activating/deactivating of the ventilatory support to the patient with respiratory effort of said patient, wherein activating/deactivating of ventilatory support comprises:
detecting a decrement of an amplitude, integral, derivative or combination thereof related to the myoelectrical signal; and
deactivating ventilatory support in response to detection of said decrement.

7. A method for triggering ventilatory support as recited in claim 6, wherein said decrement detection comprises:

multiplying a current sample of the myoelectrical signal by a predetermined constant to produce a multiplied sample;

comparing the multiplied sample to a preceding sample of the myoelectrical signal; and detecting said decrement when the amplitude, integral, derivative or combination thereof related to the multiplied sample is smaller than the amplitude, integral, derivative or combination thereof related to the preceding sample.

8. A method for triggering ventilatory support as recited in any one of claims 1, 3, 5, or 6, further comprising:

detecting a level of noise in the myoelectrical signal; and determining whether the respiratory-related muscle of the patient is active in relation to the detected level of noise.

9. A method for triggering ventilatory support as recited in any one of claims 1, 3, 5, or 6, wherein:

sensing myoelectrical activity comprises sensing myoelectrical activity of the respiratory-related muscle on two opposite sides of the center of a depolarizing region of said respiratory-related muscle; and calculating a real-time myoelectrical signal comprises:

generating two myoelectrical signal components in response to sensing of the myoelectrical activity of the respiratory-related muscle on the two opposite sides of the center:of the depolarizing region, respectively, said two myoelectrical signal components having reversed polarities;

subtracting the two myoelectrical signal components from each other to produce a subtraction signal;

adding the two myoelectrical signal components to each other to produce an addition signal;

comparing the addition signal to the subtraction signal; and accepting the subtraction signal as real-time myoelectrical signal in relation to the comparison between the addition signal and the subtraction signal.

10. A method for triggering ventilatory support as recited in claim 9, wherein the subtraction signal, the addition signal, the multiplied addition-signal and the myoelectrical signal comprise RMS signals.

11. A method for triggering ventilatory support as recited in claim 9, wherein:

comparing the addition signal to the subtraction signal comprises multiplying the addition signal by a predetermined constant to produce a multiplied addition signal, and comparing the multiplied addition signal to the subtraction signal; and accepting the subtraction signal as real-time myoelectrical signal comprises accepting the subtraction signal as real-time myoelectrical signal when the subtraction signal has an amplitude, integral, derivative or combination thereof higher than an amplitude, integral, derivative or combination thereof related to the multiplied addition signal.

12. A method for triggering ventilatory support as in any of claims 1, 3, 5 or 6, further comprising:

measuring respiratory flow of the patient, and producing a respiratory flow signal;

measuring respiratory pressure of the patient, and producing a respiratory pressure signal; and activating ventilatory support in relation to the myoelectrical signal, respiratory flow signal and/or respiratory pressure signal to assist respiration of the patient in response to respiratory effort of said patient.

13. A device for triggering ventilatory support from a ventilatory apparatus connected to a patient's respiratory-system to assist respiration of said patient, comprising:

sensor means for sensing myoelectrical activity of a respiratory-related muscle of the patient, to thereby detect respiratory effort of said patient;

means for calculating, in response to the sensed muscle myoelectrical activity, a real-time myoelectrical signal representative of a level or change in respiratory effort; and means for activating/deactivating ventilatory support in relation to the myoelectrical signal to synchronise, in real-time, activating/deactivating of the ventilatory support to the patient with respiratory effort of said patient, said activating/deactivating means comprising:

means for comparing an amplitude, integral, derivative or combination thereof related to the myoelectrical signal to a given threshold; and means for activating ventilatory support when said amplitude, integral, derivative or combination thereof is higher than said given threshold.

14. A device for triggering ventilatory support as recited in claim 13, further comprising means for filtering from the myoelectrical signal at least one of the following disturbances: motion artifacts, ECG, electrical interference, and high frequency noise.

15. A device for triggering ventilatory support from a ventilatory apparatus connected to a patient's respiratory system to assist respiration of said patient, comprising:

sensor means for sensing myoelectrical activity of a respiratory-related muscle of the patient, to thereby detect respiratory effort of said patient;

means for calculating, in response to the sensed muscle myoelectrical activity, a real-time myoelectrical signal representative of a level or change in respiratory effort; and means for activating/deactivating ventilatory support in relation to the myoelectrical signal to synchronise, in real-time, activating/deactivating of the ventilatory support to the patient with respiratory effort of said patient, wherein the activating/deactivating means comprises:

means for detecting an increment of an amplitude, integral, derivative or combination thereof related to the myoelectrical signal; and means for activating ventilatory support in response to detection of said increment.

16. A device for triggering ventilatory support as recited in claim 15, wherein the increment detecting means comprises:

means for multiplying a current sample of the myoelectrical signal by a predetermined constant to produce a multiplied sample;

means for comparing the multiplied sample to a preceding sample of the myoelectrical signal; and means for detecting said increment when the amplitude, integral, derivative or combination thereof related to the multiplied sample is higher than the amplitude, integral, derivative or combination thereof related to the preceding sample.

17. A device for triggering ventilatory support from a ventilatory apparatus connected to a patient's respiratory system to assist respiration of said patient, comprising:

sensor means for sensing myoelectrical activity of a respiratory-related muscle of the patient, to thereby detect respiratory effort of said patient;

means for calculating, in response to the sensed muscle myoelectrical activity, a real-time myoelectrical signal representative of a level or change in respiratory effort; and means for activating/deactivating ventilatory support in relation to the myoelectrical signal to synchronise, in real-time, activating/deactivating of the ventilatory support to the patient with respiratory effort of said patient, wherein the activating/deactivating means comprises:

means for comparing an amplitude, integral, derivative or combination thereof related to the myoelectrical signal to a given threshold; and means for deactivating ventilatory support when said amplitude, integral, derivative or combination thereof is lower than said given threshold.

18. A device for triggering ventilatory support from a ventilatory apparatus connected to a patient's respiratory system to assist respiration of said patient, comprising:

sensor means for sensing myoelectrical activity of a respiratory-related muscle of the patient, to thereby detect respiratory effort of said patient;

means for calculating, in response to the sensed muscle myoelectrical activity, a real-time myoelectrical signal representative of a level or change in respiratory effort; and means for activating/deactivating ventilatory support in relation to the myoelectrical signal to synchronise, in real-time, activating/deactivating of the ventilatory support to the patient with respiratory effort of said patient, wherein the activating/deactivating means comprises:

means for detecting a decrement of an amplitude, integral, derivative or combination thereof related to the myoelectrical signal; and means for deactivating the ventilatory support in response to detection of said decrement.

19. A device for triggering ventilatory support as recited in claim 18, wherein said decrement detecting means comprises:

means for multiplying a current sample of the myoelectrical signal by a predetermined constant to produce a multiplied sample;

means for comparing the multiplied sample to a preceding sample of the myoelectrical signal; and means for detecting said decrement when the amplitude, integral, derivative or combination thereof related to the multiplied sample is smaller than the amplitude, integral, derivative or combination thereof related to the preceding sample.

20. A device for triggering ventilatory support as recited in any one of claims 13, 15, 17, or 18 further comprising:

means for detecting a level of noise in the myoelectrical signal; and means for determining whether the respiratory-related muscle of the patient is active in relation to the detected level of noise.

21. A device for triggering ventilatory support as recited in any one of claims 13, 15, 17 or 18, wherein:

the muscle myoelectrical activity sensing means comprises means for detecting myoelectrical activity of the respiratory-related muscle on two opposite sides of the center of a depolarizing region of said respiratory-related muscle; and the real-time myoelectrical signal calculating means comprises:

means for generating two myoelectrical signal components in response to sensing of the myoelectrical activity of the respiratory-related muscle on the two opposite sides of the center of the depolarizing region, respectively, said two myoelectrical signal components having reversed polarities;

means for subtracting the two myoelectrical signal components from each other to produce a subtraction signal;

means for adding the two myoelectrical signal components to each other to produce an addition signal;

means for comparing the addition signal to the subtraction signal; and means for accepting the subtraction signal as the real-time myoelectrical signal in relation to the comparison between the addition signal and the subtraction signal.

22. A device for triggering ventilatory support as recited in claim 21, wherein the subtraction signal, the addition signal, the multiplied addition signal and the myoelectrical signal comprise RMS signals.

23. A device for triggering ventilatory support as recited in claim 21, wherein:

the means for comparing the addition signal to the subtraction signal comprises means for multiplying the addition signal by a predetermined constant to produce a multiplied addition signal, and means for comparing the multiplied addition signal to the subtraction signal; and the accepting means comprises means for accepting the subtraction signal as real-time myoelectrical signal when the subtraction signal has an amplitude, integral, derivative or combination thereof higher than an amplitude, integral, derivative or combination thereof related to the multiplied addition signal.

24. A device for triggering ventilatory support as in any of claims 13, 15, 17, or 18, further comprising:

a respiratory flow detector for measuring respiratory flow of the patient, and producing a respiratory flow signal;

a respiratory pressure detector for measuring respiratory pressure of the patient, and producing a respiratory pressure signal; and a logic trigger circuit for triggering ventilatory support in relation to the myoelectrical signal, respiratory flow signal and/or respiratory pressure signal to assist respiration of the patient in response to respiratory effort of said patient.

* * * * *